US005104988A

United States Patent [19]

Ohkawa

[11] Patent Number: 5,104,988
[45] Date of Patent: Apr. 14, 1992

[54] 4'-ALKOXY-2,2':6',2''-TERPYRIDINE DERIVATIVES AND METAL COMPLEXES THEREOF

[75] Inventor: Atsuhiro Ohkawa, Kanagawa, Japan

[73] Assignee: Fuji Photo Film Co., Ltd., Kanagawa, Japan

[21] Appl. No.: 537,953

[22] Filed: Jun. 13, 1990

[30] Foreign Application Priority Data

Feb. 12, 1988 [JP] Japan .................................. 63-28897
Jul. 19, 1988 [JP] Japan .................................. 63-178097

[51] Int. Cl.$^5$ ..................... C07F 15/02; C07F 15/04; C07F 15/06; C07F 15/00
[52] U.S. Cl. ................................................. 546/2
[58] Field of Search ............................................. 546/2

[56] References Cited

U.S. PATENT DOCUMENTS 4,598,030  7/1986  Reczek .................................. 546/2

OTHER PUBLICATIONS

"Chemical Dictionary", (Tokyo Kaga Dojin, 1989) p. 164.

*Primary Examiner*—Mark L. Berch
*Attorney, Agent, or Firm*—Sughrue, Mion, Zinn Macpeak & Seas

[57] ABSTRACT

4'-alkoxy-2,2':6',2'''-terpyridine derivatives of formula (I) and metal complexes thereof of formula (II).

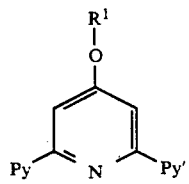

where $R^1$ represents a substituted or unsubstituted alkyl group, wherein the substituent is a member selected from the group consisting of an aryl group, a heterocyclic group bonded to the alkyl group via the carbon atom thereof, an alkoxy group, an aryloxy group, an alkylthio group and an arylthio group; Py and Py' each represent a substituted or unsubstituted 2-pyridyl group.

$$M(Lig1)x(Lig2)y(A)z \quad (II)$$

where M is a metal ion;
Lig1 is the compound of formula (I):
Lig2 is a ligand to the metal ion M, except Lig1;
A is a counter ion to M(Lig1)x(Lig2)y;
x is an integer of 1 or 2; and
y and z each are an integer of from 0 to 6.

The metal complexes (II) are useful as dyes having high wet heat-fastness.

3 Claims, No Drawings

4'-ALKOXY-2,2':6',2"-TERPYRIDINE DERIVATIVES AND METAL COMPLEXES THEREOF

This is a division of application Ser. No. 309,649, filed Feb. 13, 1989, now U.S. Pat. No. 4,960,895.

FIELD OF THE INVENTION

The present invention relates to 4'-alkoxy-substituted 2,2':6',2"-terpyridine derivatives which are useful as a ligand for various metals and which have, in the form of a metal complex thereof, photo-catalytic activity and physiological activity. More precisely, the present invention relates to 4'-alkoxy-2,2':6',2"-terpyridine derivatives capable of forming stable an highly heat-fast dyes with various metals as well as to metal complexes of such derivatives.

BACKGROUND OF THE INVENTION

Unsubstituted 2,2':6',2"-terpyridine is known to be an effective ligand for various metals. Most metal complexes thereof have heretofore been widely studied not only in the field of ligand chemistry but also in the field of analytical chemistry as they display various colors.

Recently, it has been found that metal complexes of 2,2':6',2"-terpyridine act as a photo-catalyst and are useful as a medium for conversion of solar energy.

On the other hand, there is almost no disclosure regarding substituted 2,2':6',2"-terpyridines in the literature (see, for instance, Abramovitch *Pyridine and Its Derivatives* (John Wiley & Sons, 1974); *Synthesis*, page 1 (1976); Otto Meth-Chon, *Comprehensive Heterocyclic Chemistry* (Pergamon Press, 1984)). Only the following compounds are known as substituted 2,2':6',2"-terpyridines.

(1) 4'-Methanesulfonyl-2,2':6',2"-terpyridine (*J. American Chemical Society*, Vol. 109, page 961, 1987)

(2) 4'-Amino-2,2':6',2"-terpyridine derivative and 4'-phenoxy-2,2':6',2"-terpyridine derivatives (U.S. Pat. Nos. 4,555;477 and 4,568,633)

2,2':6',2"-terpyridine derivatives where the 4'-position is substituted by an unsubstituted alkoxy group or an alkoxy group substituted by an aryl group, a heterocyclic group bonded via the carbon atom, an alkoxy group, an aryloxy group, an alkylthio group or an arylthio group are quite unknown up to the present.

On the other hand, development of dyes having a high wet heat-fastness is desired in the field of dyes.

SUMMARY OF THE INVENTION

In accordance with the present invention there are provided 4'-alkoxy-2,2':6',2"-terpyridine derivatives of general formula (I):

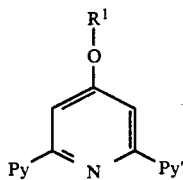

(I)

where $R^1$ represents a substituted or unsubstituted alkyl group, wherein the substituent is a member selected from the group consisting of an aryl group, a heterocyclic group bonded to the alkyl group via the carbon atom thereof, an alkoxy group, an aryloxy group, an alkylthio group and an arylthio group; Py and Py' each represent a substituted or unsubstituted 2-pyridyl group.

There are further provided dyes with a high wet heat-fastness, which are represented by the general formula (II):

M(Lig1)x(Lig2)y(A)z    (II)

where M represents a metal ion;
Lig1 represents a compound as represented by the aforesaid formula (I);
Lig2 represents a ligand to the metal ion M, except Lig1;
A represents a counter ion to M(Lig1)x(Lig2)y;
x represents an integer of 1 or 2; and
y and z each represents an integer of from 0 to 6.

DETAILED DESCRIPTION OF THE INVENTION

The compounds of formula (I) of the present invention will be explained in detail hereunder.

In the compounds of formula (I), $R^1$ is especially preferably a primary alkyl group (e.g., methyl, ethyl, propyl, butyl, pentyl, hexyl, octyl, nonyl, decyl, undecyl, dodecyl, tridecyl, tetradecyl, pentadecyl, hexadecyl, octadecyl, nonadecyl, eicosyl, 2-methoxyethyl, (2'methoxy)-2-ethoxymethyl, 3-mercaptomethylpropyl, 4-ethylhexyl, benzyl or 2-phenylethyl), a secondary alkyl group (e.g., isopropyl, 3-octyl, cyclohexyl or 1-phenylethyl) or a tertiary alkyl group (e.g., 2-methyl-2-propyl or 2-phenyl-2-propyl).

Among them, especially preferred are those where the number of the total carbon atoms in $R^1$ is from 1 to 18, particularly preferably from 2 to 16.

In formula (I), Py and Py' may be substituted by a variety of substituent(s). Preferred substituents include, for example, an alkyl group (e.g., methyl, ethyl, hexyl, decyl, isopropyl, t-butyl), an aryl group (e.g., phenyl, 1-naphthyl), a heterocyclic group (e.g., 4-pyridyl, 2-pyridyl, 1-pyrrolidinyl, 3-tetrahydrofuryl), an alkenyl group (e.g., vinyl, 1-propenyl, cinnamyl), an alkynyl group (e.g., 1-propynyl, phenylethynyl), an alkoxy group (e.g., methoxy, butoxy, decyloxy, isopropoxy, t-butoxy), an aryloxy group (e.g., phenoxy, 1-naphthoxy, 2-naphthoxy), a heterocyclic-oxy group (e.g., 3-pyridinyloxy, 4-(N-methylpyrrilidinyl)oxy, 3-tetrahydrofuranoxy), an amino group (e.g., dimethylamino, dibutylamino, methylphenylamino), a carbamoyl group (e.g., N,N-dimethylcarbamoyl, N-methylN-phenylcarbamoyl), an alkylthio group (e.g., methylthio, butylthio, decylthio, isopropylthio, t-butylthio), an arylthio group (e.g., phenylthio, 1-naphthylthio, 2-naphthylthio), a heterocyclic-thio group (e.g., 2-pyridylthio, 3-pyridylthio), an alkylsulfinyl group (e.g., methanesulfinyl, butanesulfinyl, decanesulfinyl, isopropylsulfinyl, t-butylsulfinyl), an arylsulfinyl group (e.g., phenylsulfinyl, 1-naphthylsulfinyl, 2-naphthylsulfinyl) and a heterocyclic-sulfinyl group (e.g., 3-pyridylsulfinyl). Py and Py' each are especi ally preferably 2-pyridyl, 6-methyl-2-pyridyl, 6-pheny-2-pyridyl, 4-methyl-2-pyridyl, 4-vinyl-2-pyridyl or 6-vinyl-2-pyridyl group.

Specific examples of the compounds of formula (I) of the present invention will be mentioned below, which, however, are not intended to restrict the scope of the present invention.

TABLE 1
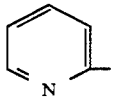
| Compound No. | R¹ | Py | Py' |
|---|---|---|---|
| T-1 | CH₃— | 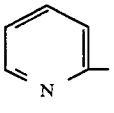 | 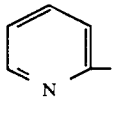 |
| T-2 | CH₃CH₂— | 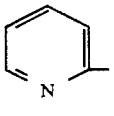 | 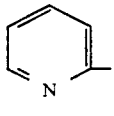 |
| T-3 | CH₃CH₂CH₂CH₂— | 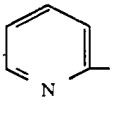 | 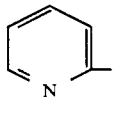 |
| T-4 | CH₃(CH₂)₃CHCH₂—<br>　　　　　\|<br>　　　　CH₃CH₂ | 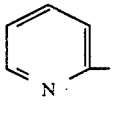 | 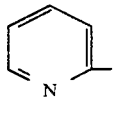 |
| T-5 | CH₃(CH₂)₇— | 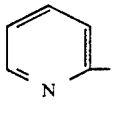 | 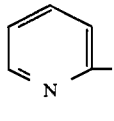 |
| T-6 | CH₃(CH₂)₁₅— | 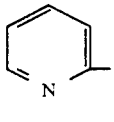 | 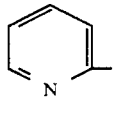 |
| T-7 | CH₃OCH₂CH₂— | 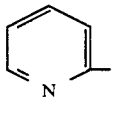 | 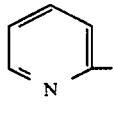 |
| T-8 | CH₃OCH₂CH₂OCH₂CH₂— | 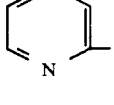 | 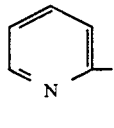 |
| T-9 | CH₃SCH₂CH₂— | 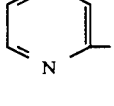 | 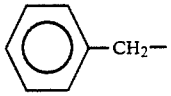 |
| T-10 | 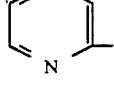 | 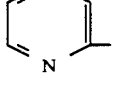 | 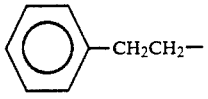 |
| T-11 | 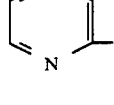 | 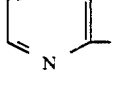 | |

TABLE 1-continued
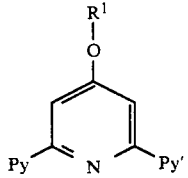
| Compound No. | R¹ | Py | Py' |
|---|---|---|---|
| T-12 | 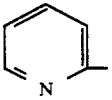 | 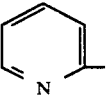 | 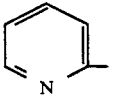 |
| T-13 | $(CH_3)_3C-$ | 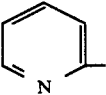 | 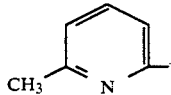 |
| T-14 | $CH_3(CH_2)_7-$ | 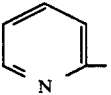 | 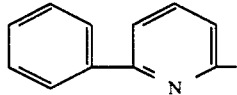 |
| T-15 | $CH_3(CH_2)_7-$ | 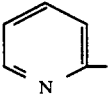 | 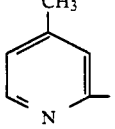 |
| T-16 | $CH_3(CH_2)_7-$ | 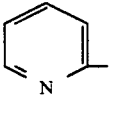 | 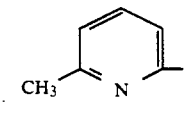 |
| T-17 | $CH_3(CH_2)_7-$ | 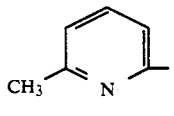 | 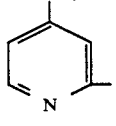 |
| T-18 | $CH_3(CH_2)_7-$ | 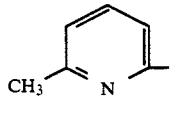 | 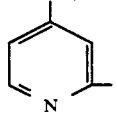 |
| T-19 | $CH_3(CH_2)_7-$ | 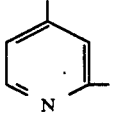 | 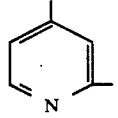 |
| T-20 | $CH_3(CH_2)_7-$ | 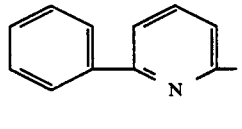 | 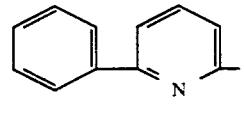 |
| T-21 | 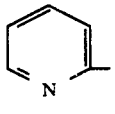 | | |

TABLE 1-continued

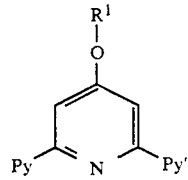

| Compound No. | R¹ | Py | Py' |
|---|---|---|---|
| T-22 | $CH_3OCH_2CH_2-$ | 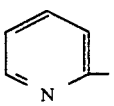 | 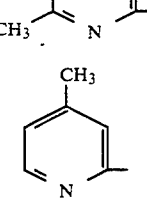 |
| T-23 | $CH_3OCH_2CH_2-$ | 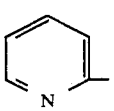 | 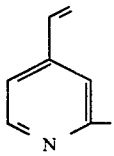 |
| T-24 | $CH_3OCH_2CH_2-$ | 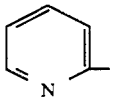 | |

In the compounds of the aforesaid formula (II), M represents a metal ion and is, preferably, $Fe^{2+}$, $Fe^{3+}$, $Ni^{2+}$, $Cu+$, $Cu^{2+}$, $Zn^{2+}$, $Co^{2+}$, $Cr^{2+}$, $Cr^{3+}$, or $Ru^{3+}$. Among them, metal ions of $Fe^{2+}$, $Ni^{2+}$, $Cu+$, $Zn^{2+}$, $Co^{2+}$ and $Ru^{3+}$ are more preferred; and especially preferred are metal ions of $Fe^{2+}$, $Cu^{2+}$, $Co^{2+}$ and $Ru^{3+}$.

Lig1 means a compound of the aforesaid formula (I).

When x is 2, two Lig1's may be the same or different, but are preferably same.

Lig2 represents a ligand to M, except Lig1. Any and every conventional ligand which is known in the field of complex chemistry may be ligand Lig2. More concretely, there are mentioned a halogen ion ($F^-$, $Cl^-$, $Br^-$, $I^-$), water, a hydroxyl ion, acetic acid, a carboxylic acid (e.g., propionic acid, benzoic acid), sulfuric acid, nitric acid, ammonia, cyane ion, an amine (ethylenediamine, 2,2'-bipyridine), an amino acid (ethylenediaminetetraacetic acid, glycine) and an amino alcohol (2-aminoethanol), as well as conjugate acids or conjugate bases of the said compounds. Among them, preferred are those which may act as a unidentate ligand to the compounds; and especially preferred are halogen ions, water, a hydroxyl ion and ammonia. When y is 2 or more, all Lig2's may be the same or different.

A represents a counter ion to the complex ion $M(Lig1)_x(Lig2)_y$. Accordingly, z is 0 in the compounds where the complex $M(Lig1)_x(Lig2)_y$ is electrically neutral. In most cases, A is derived from the kinds of the metal salts which are the raw materials for production of the complex (or that is, the counter anion of the metal ion). The complexes of formula (II) may be subjected to chemical or physical ion-exchange.

z represents an integer of from 0 to 6, and when z is 2 or more, all A's may be the same or different.

Specific examples of the compounds of formula (II) of the present invention will be mentioned below, which, however, are not intended to restrict the scope of the present invention.

TABLE 2

| Compound No. | M | Lig1 | x | Lig2 | y | A | z |
|---|---|---|---|---|---|---|---|
| C-1 | $Fe^{2-}$ | T-4 | 2 | — | 0 | $Cl^-$ | 2 |
| C-2 | $Fe^{2+}$ | T-6 | 2 | — | 0 | $Cl^-$ | 2 |
| C-3 | $Fe^{2+}$ | T-7 | 2 | — | 0 | $Cl^-$ | 2 |
| C-4 | $Fe^{2+}$ | T-9 | 2 | — | 0 | $Cl^-$ | 2 |
| C-5 | $Fe^{2+}$ | T-10 | 2 | — | 0 | $Cl^-$ | 2 |
| C-6 | $Fe^{2+}$ | T-20 | 2 | — | 0 | $Cl^-$ | 2 |
| C-7 | $Fe^{2+}$ | T-6 | 1 | $H_2O$ | 1 | — | 0 |
|  |  |  |  | $Cl^-$ | 2 |  |  |
| C-8 | $Fe^{3+}$ | T-6 | 2 | — | 0 | $Cl^-$ | 3 |
| C-9 | $Fe^{3+}$ | T-9 | 2 | — | 0 | $Cl^-$ | 3 |
| C-10 | $Fe^{2+}$ | T-3 | 2 | — | 0 | $Cl^-$ | 2 |
| C-11 | $Ni^{2+}$ | T-6 | 2 | — | 0 | $Cl^-$ | 2 |
| C-12 | $Ni^{2+}$ | T-6 | 2 | — | 0 | $\frac{1}{2}SO_4^{2-}$ | 2 |
| C-13 | $Cu^{2+}$ | T-4 | 2 | — | 0 | $SO_4^{2-}$ | 2 |
| C-14 | $Cu^{2+}$ | T-4 | 2 | — | 0 | $Cl^-$ | 2 |
| C-15 | $Cu^{2+}$ | T-7 | 2 | — | 0 | $NO_3^-$ | 2 |
| C-16 | $Cu+$ | T-4 | 2 | — | 0 | $Br^-$ | 1 |
| C-17 | $Zn^{2+}$ | T-4 | 2 | — | 0 | $Cl^-$ | 2 |
| C-18 | $Zn^{2+}$ | T-4 | 1 | $H_2O$ | 1 | — | 0 |
|  |  |  |  | $Cl^-$ | 2 |  |  |
| C-19 | $Zn^{2+}$ | T-7 | 2 | — | 0 | $SO_4^{2-}$ | 2 |
| C-20 | $Zn^{2+}$ | T-19 | 2 | — | 0 | $Cl^-$ | 2 |
| C-21 | $Co^{2+}$ | T-4 | 2 | — | 0 | $Br^-$ | 2 |
| C-22 | $Co^{2+}$ | T-4 | 2 | — | 0 | $CH_3CO_2^-$ | 2 |
| C-23 | $Co^{2+}$ | T-7 | 2 | — | 0 | $Cl^-$ | 2 |
| C-24 | $Co^{2+}$ | T-17 | 2 | — | 0 | $Cl^-$ | 2 |
| C-25 | $Ru^{3+}$ | T-4 | 2 | — | 0 | $Cl^-$ | 3 |
| C-26 | $Ru^{3+}$ | T-6 | 2 | — | 0 | $Cl^-$ | 3 |
| C-27 | $Ru^{3+}$ | T-7 | 2 | — | 0 | $Cl^-$ | 3 |

Now, production of the compounds of the persent invention will be mentioned hereunder. The present invnetion has been attained by development of the following methods for producing the new compounds of the present invention.

Specifically, the compounds of formula (I) of the present invention can be produced in accordance with the step of either scheme-1 or scheme-2 below.

Scheme-1:

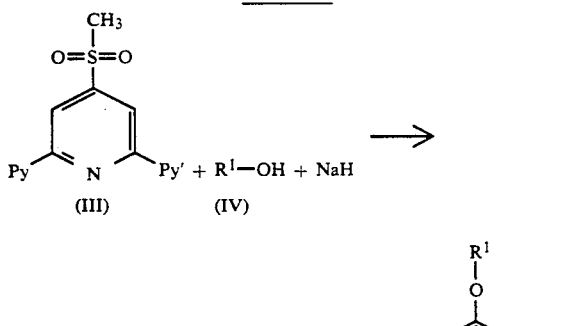

Scheme-2:

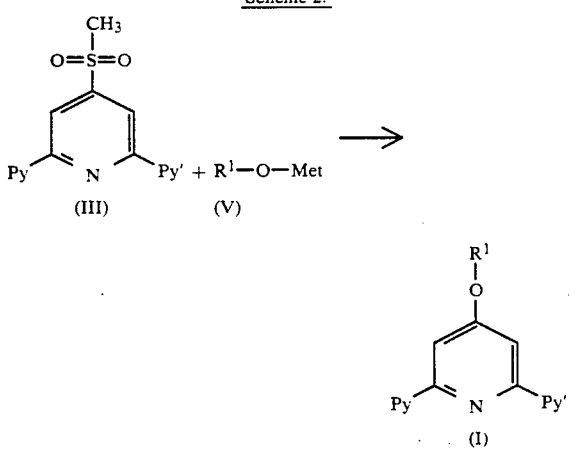

In formulae (III) to (V) in the aforesaid reaction schemes, R¹, Py and Py' have the same meanings as those in formula (I); and Met represents lithium, sodium or potassium. Among the two reaction schemes for producing the compounds of formula (I), the method of reaction scheme-is first discussed in detail below. The compound of formula (III) can be produced in accordance with the method described in *J. Orq. Chem.*, Vol. 47, page 3028 (1982) or *J. Am. Chem. Soc.*, Vol. 109, page 3961 (1987).

The compound of formula (I) can be obtained by reacting the compound of formula (III) and the compound of formula (IV) in the presence of a base. As the base for the reaction, sodium hydride, lithium hydride or potassium hydride is preferred.

As the reaction solvent, dimethylformamide, dimethylacetamide, dimethylsulfoxide, acetonitrile, tetrahydrofuran, 1,2-dimethoxyethane, dioxane or diethylene glycol dimethyl ether is preferred. The solvents may be used singly or in the form of a mixture of two or more of them. The reaction temperature is suitable from 30° C. to 200° C., more preferably from 50° C. to 190° C.

Next, the method of the reaction scheme-2 will be explained in detail below.

The compound of the formula (III) is the same as that referred to in reaction scheme-1. The compound of formula (V) can easily be prepared by reacting the corresponding alcohol where Met in formula (V) is substituted by hydrogen and an organic metal reagent such as butyl lithium or a simple metal substance such as lithium, sodium or potassium. The thus prepared compound of formula (V) is reacted with the compound of formula (III) in the same solvent as that referred to for reaction scheme-1 under the same reaction temperature condition as that referred to for reaction scheme-1, whereby the compound of the formula (I) can be obtained.

Now, production of the metal complexes of the formula (II) of the present invention will be mentioned below.

The complexes of formula (II) can easily be produced by blending a metal salt and the terpyridine derivative of formula (I) in a solvent, optionally under heat. As the solvent for the reaction, a protonic solvent such as methanol, ethanol or water is preferred. As the case may be, a solvent such as tetrahydrofuran, dioxane, acetonitrile, acetone or chloroform, or a mixed solvent comprising these solvents and the above-mentioned protonic solvent is preferred to the single protonic solvent so as to yield a higher yield. Most of the complexes thus prepared are crystalline, and they can be purified by recrystallization or reprecipitation.

The 4'-alkoxy-2,2':6',2''-terpyridine derivatives of the formula (I) of the present invention have various advantageous merits as mentioned below.

(1) Using readily available 4'-methanesulfonyl-2,2':6',2''-terpyridine, 4'-alkoxy-2,2':6',2''-terpyridines can be provided with high yield.

(2) 4'-Alkoxy-2,2':6',2''-terpyridines which have been heretofore unavailable can be provided (3) 4'-Alkoxy-2,2':6',2''-terpyridines which are expected to express excellent functions as a photocatalyst or physiological active substance can be provided.

(4) Substantially magenta-coloring complex dyes can be produced by reacting the 4'-alkoxy-2,2':6',2''-terpyridine of the invention and a metal salt.

The 4'-alkoxy-2,2':6',2''-terpyridine metal complexes of formula (II) of the invention also have various advantageous merits as mentioned below.

(5) From a 4'-alkoxy-2,2':6',2''-terpyridine and a metal salt, the corresponding metal complex can be produced with ease and with high yield.

(6) 4'-Alkoxy-2,2':6',2''-terpyridine metal complexes excellent in wet heat-fastness can be provided.

(7) 4'-Alkoxy-2,2':6',2''-terpyridine metal complexes useful as a dye can be provided.

(8) 4'-Alkoxy-2,2':6',2:-terpyridine metal complexes, in which the center metal may be varied to give dyes each having a different $\lambda_{max}$ of from 400 nm to 800 nm, can be provided.

The dyes thus prepared in accordance with the present invention can be utilized in image formation in diffusion transfer process and can also be used as a filter dye, an anti-halation dye or a coating paint.

The following examples are intended to illustrate the present invention but not to limit it in any way.

EXAMPLE 1

Production of 4'-Hexadecyl-2,2':6',2''-terpyridine

4'-Methanesulfonyl-2,2':6',2''-terpyridine (4.67 g, 0.015 mol) and hexadecyl alcohol (2,42 g, 0.010 mol) were added to N,N-dimethylformamide (0.1 liter). At 15° C., sodium hydride (60% content, oil dispersion, 0.8 g) was added thereto over a period of about 10 minutes. The entire solution was stirred for 30 minutes and then the reaction mixture was reacted under reflux for 4 hours. After cooling to room temperature, the reaction mixture was poured into an aqueous 4M sodium chloride solution (0.3 liter). The crystal that precipitated was taken out by filtration under suction and then washed with water and hexane. The crystal was again dissolved in chloroform and washed with 1M hydrochloric acid and water. The organic layer was dried over anhydrous sodium sulfate and then concentrated. The resulting crystal was recrystallized from hexane to obtain 4.36 g of the above-entitled product (T-6). Yield: 92%. m.p. 97.5 to 99.0° C.

EXAMPLE 2

Production of 4'-(2-Ethylhexyloxy)-2,2':6',2''-terpyridine

Sodium hydride (60% content, oil dispersion, 0.80 g) was added to a mixture of 4'-methanesulfonyl-2,2':6',2''-terpyridine (4.67 g, 0.015 mol) and 2-ethyl-1-hexanol (1.30 g, 0.010 mol) over a period of about 10 minutes. After stirring for 30 minutes at room temperature, the reaction mixture was refluxed and further reacted for 4 hours. After cooling to room temperature, the reaction mixture was poured into an aqueous 4M sodium chloride solution (0.3 liter). The crystal that precipitated was taken out by filtration under suction and then washed with water and hexane. The crystal was dried under reduced pressure (0.1 mm Hg) and then recrysalized from hexane to obtain 3.07 g of the above-entitled product (T-4) as a white crystal. Yield: 85%. m.p. 58.5° C.

EXAMPLE 3

Production of 4'-(2-Methoxyethoxy)-2,2':6',2''-terpyridine

Sodium hydride (60% content, oil dispersion, 1.20 g, 0.030 mol) was added to a mixture of 4'-methanesulfonyl-2,2':6',2''-terpyridine (3.11 g, 0.010 mol), 2-methoxyethanol (1.14 g, 0.015 mol) and DMF (0.1 liter) over a period of 10 minutes and then stirred for another 30 minutes. Thereafter, the reaction mixture was refluxed for 3 hours and then cooled to room temperature. The reaction mixture was then poured into an aqueous 4M sodium chloride solution and the crystal that precipitated was taken out by filtration under suction and then washed with water and hexane The crystal thus taken out was purified by passing the same into an alumina column using chloroform as an eluent, whereby 2.92 g of the above-entitled product (T-7) was obtained. Yield: 95%. m.p. 105.0 to 105.5° C.

EXAMPLE 4

Production of 6-Phenyl-4'-benzyloxy-2,2':6',2''-terpyridine

Sodium hydride (60% content, oil dispersion, 0.8 g) was added to a mixture of 6-phenyl-4'-methanesulfonyl-2,2':6',2''-terpyridine (4.67 g, 0.015 mol), benzyl alcohol (1.08 g, 0.010 mol) and N,N-dimethylformamide (0.1 liter) over a period of 10 minutes. The reaction solution was refluxed for 6 hours and then processed in the same manner as in Example 1, whereby 2.88 g of the above-entitled product (T-21) was obtained. Yield: 85%. m.p. 182° C.

EXAMPLE 5

Production of Metal Complex (C-2)

4'-Hexadecyloxy-2,2':'6',2''-terpyridine (130 mg, 0.28 mmol) and ferrous chloride dihydrate (20 mg, 0.14 mmol) were refluxed in ethanol (10 ml) for 1 hour. The reaction mixture was cooled to room temperature and then the solvent was removed by vacuum distillation. The residue was reprecipitated from chloroform/hexane (1:5) to obtain 142 mg of bis(4'-hexadecyloxy-2,2':6',2''-terpyridine)iron(II) chloride as a magenta-colored complex. $\lambda_{max}$: 559 nm, $\epsilon = 1.22 \times 10^4$ (measured in chloroform).

EXAMPLE 6

Production of Metal Complex (C-3)

4'-Methoxyethoxy-2,2':6',2''-terpyridine (0.31 g, 1.0 mmol) and ferrous chloride dihydrate (71 mg, 0.5 mmol) were refluxed in methanol (15 ml) for 30 minutes. The reaction mixture was cooled to room temperature and then the solvent was removed by vacuum distillation. The residue was reprecipitated from chloroform/hexane (1:5) to obtain 0.36 g of metal complex (C-3). $\lambda_{max}$: 560 nm, $\epsilon = 1.13 \times 10^4$ (measured in chloroform).

EXAMPLE 7

Production of Metal Complex (C-7)

A mixture comprising 4'-hexadecyloxy-2,2':6',2'''-terpyridine (0.13 g, 1.28 mmol), ferrous chloride dihydrate (44 mg, 0.30 mmol) and ethanol (10 ml) was heated and stirred for 1 hour Then the reaction mixture was processed in the same manner as in Example 5 to obtain 0.15 g of metal complex (C-7). $\lambda_{max}$: 558 nm, $\epsilon = 0.61 \times 10^4$ (measured in chloroform).

EXAMPLE 8

Production of Metal Complex (C-15)

4'-Methoxyethoxy 2,2':6',2''-terpyridine (0.31 g, 1 mmol) and cupric nitrate 2.5-hydrate (0.11 g, 0.5 mmol) were suspended in ethanol (15 ml) and refluxed for 1 hour. After the reaction mixture was cooled to room temperature, the solvent was removed by vacuum distillation, whereby 0.38 g of metal complex (C-15) was obtained. $\lambda_{max}$: 715 nm, $\epsilon = 3.8 \times 10^3$ (measured in methanol).

EXAMPLE 9

Production of Metal Complex (C-22)

4'-(2-Ethylhexyloxy)-2,2':6',2''-terpyridine (0.36 g, 1 mmol) and cobalt(II)acetate 4-hydrate (0.12 g, 0.5 mmol) were suspended in ethanol (15 ml) and refluxed for 1 hour. Then the reaction mixture was processed in the same manner as in Example 8 to obtain 0.46 g of metal complex (C-22). $\lambda_{max}$: 415 nm, $\epsilon = 2.1 \times 10^3$ (measured in methanol).

EXAMPLE 10

Wet Heat-fastness of Dyes

The wet heat-fastness of the dyes of the present invention was determined under two conditions of (A) 60° C. and 70% RH for 8 weeks and (B) 100° C. and 15% RH for 16 days. For the experiment, the dye to be tested was allowed to stand in either of the conditions in the form of a powder, and the residual percentage of the dye was determined by high performance liquid chromatography or the absorptiometry. As a comparative sample for the fastness, Dye D-1 mentioned below was used.

The residual percentage of the dye as stored under the condition of 60° C. and 70% RH for 8 weeks and that as stored under the condition of 100° C., 15% RH for 16 days are shown in Table 3 below.

TABLE 3

| Dye Tested | Residual Percentage of Dye | |
|---|---|---|
| | 60° C., 70% RH, 8 weeks (%) | 100° C., 15% RH, 16 days (%) |
| C-2 | 99 | 97 |
| C-3 | 98 | 96 |
| C-6 | 99 | 95 |
| C-13 | 99 | 95 |
| C-21 | 98 | 97 |
| C-25 | 99 | 96 |
| D-1 (Comparison) | 69 | 45 |

From the results in Table 3 above, the dyes of the present invention were found to be extremely stable to humidity and heat.

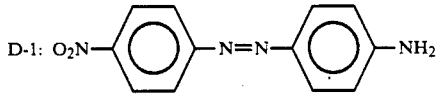

EXAMPLE 11

The following layers were coated on a cellulose triacetate film support to obtain a film sample.

| First Layer: | |
|---|---|
| Gelatin | 1.2 g |
| T-4 | 5 × 10⁻⁴ mol |
| Dibutyl phthalate | 0.30 g |
| Second Layer: | |
| Gelatin | 0.9 g |
| Polymethyl methacrylate grains (diameter 1.5 um) | 0.4 g |
| Hardening agent H-1 | 0.8 g |

The film sample thus prepared was cut into a 35 mm width and dipped in either solution-1 or solution-2 (38° C.) mentioned below for 3 minutes, whereby an iron or cobalt complex was formed in the film. The samples were called Sample-1 and Sample-2, respectively.

| Solution | Composition | Concentration (mol/liter) |
|---|---|---|
| 1 | Ammonium Iron(II) Sulfate Hexahydrate | 1 × 10⁻² |
| 2 | Cobalt(II) Chloride | 1 × 10⁻² |

For comparison, Comparative Sample-3 was prepared in the same manner except that the dye D-2 was used in place of the alkoxy-terpyridine (T-4).

The thus prepared film Samples 1, 2 and 3 were stored under the condition of 60° C. and 70% RH for 8 weeks or under the condition of 100° and 15% RH for 16 days, whereby the stability of the dye in each sample was tested.

The results obtained are shown in Table 4 below.

TABLE 4

| Sample | Dye | Residual Percentage of Dye | | |
|---|---|---|---|---|
| | | 60° C., 70% RH, 8 weeks (%) | 100° C., 15% RH, 16 days (%) | |
| 1 | T-4/Fe²⁺ Complex | 98 | 96 | Invention |
| 2 | T-4/Co²⁺ Complex | 98 | 95 | Invention |
| 3 | D-2 | 85 | 60 | Comparison |

From the results in Table 4, it is noted that the dyes of the present invention are superior to indoaniline dye D-2 with respect to the heat-fastness.

The compounds used in the example had the following structural formulae.

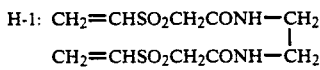

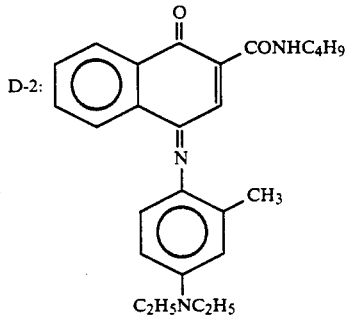

While the invention has been described in detail and with reference to specific embodiments thereof, it will be apparent to one skilled in the art that various changes and modifications can be made therein without departing from the spirit and scope thereof.

What is claimed is:

1. A metal complex of formula (II):

$$M(Ligl)_x(A)_2 \qquad (II)$$

where M represents a metal ion selected from the group consisting of $Fe^{2+}$, $Fe^{3+}$, $Cu^+$, $Cu^{2+}$, $Zn^{2+}$, $Co^{2+}$, $Cr^{2+}$, $Cr^{3+}$ and $Ru^{3+}$ Ligl is a 4'-alkoxy-2.2':6',2''-terpyridine derivative of formula (I):

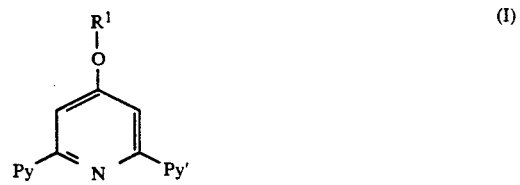

where $R^1$ represents a primary alkyl group selected from the group consisting of methyl, ethyl, propyl, butyl, pentyl, hexyl, octyl, nonyl, decyl, undecyl, dodecyl, tridecyl, tetradecyl, pentadecyl, hexadecyl, octadecyl, nonadecyl, eicosyl, 2-methoxyethyl, (2'-methoxy)-2-ethoxymethyl, 3-mercaptomethylpropyl, 4-ethylhexyl, benzyl or 2-phenylethyl; a secondary alkyl group selected from the group consisting of iospropyl, 3-octyl, cyclohexyl and 1-phenylethyl; or a tertiary alkyl group selected from the group consisting of 2-methyl-2-propyl and 2-phenyl-2-propyl; Py and Py' each represent a group selected from the group consisting of 2-pyridyl, 6-methyl-2-pyridyl, 6-phenyl-2-pyridyl, 4-methyl-2-pyridyl, 4-vinyl-2-pyridyl and 6-vinyl-2-pyridyl;

A represents $Cl^\ominus$, $SO_4{}^{2\ominus}$, $NO_3{}^\ominus$, $Br^\ominus$ or $CH_3CO_2{}^\ominus$;

x is 2; and z represents the number of counter ions A necessary for the compound of formula (II) to form a neutral molecule and is an integer of from 0 to 3.

2. The metal complex as claimed in claim 1, wherein M represents a metal ion selected form the group consisting of $FE^{2+}$, $Ni^{2+}$, $Cu^+$, $ZN^{2+}$, $Co^{2+}$ and $Ru^{3+}$.

3. The metal complex as claimed in claim 1, wherein M represents a metal ion selected from the group consisting of $FE^{2+}$, $Cu^{2+}$, $Co^{2+}$ and $Ru^{3+}$.

* * * * *